United States Patent
Chou

(10) Patent No.: US 10,948,741 B2
(45) Date of Patent: Mar. 16, 2021

(54) NASAL MASK STRUCTURE FOR EYEGLASSES

(71) Applicant: HSIEN CHANG OPTICAL INDUSTRIAL CO., LTD., Tainan (TW)

(72) Inventor: Wen-Hsiung Chou, Tainan (TW)

(73) Assignee: Hsien Chang Optical Industrial Co., Ltd., Tainan (TW)

( * ) Notice: Subject to any disclaimer, the term of this patent is extended or adjusted under 35 U.S.C. 154(b) by 92 days.

(21) Appl. No.: 16/218,846

(22) Filed: Dec. 13, 2018

(65) Prior Publication Data

US 2020/0192119 A1 Jun. 18, 2020

(51) Int. Cl.
*G02C 5/12* (2006.01)
*A61F 9/02* (2006.01)
*G02C 11/00* (2006.01)

(52) U.S. Cl.
CPC .............. *G02C 5/126* (2013.01); *A61F 9/029* (2013.01); *G02C 11/00* (2013.01)

(58) Field of Classification Search
CPC . G02C 7/104; G02C 7/10; G02C 7/12; G02C 7/101; G02C 7/105; G02C 7/16; G02C 2202/16; G02C 11/10; G02C 3/003; G02C 7/02; G02C 2200/02; G02C 7/108; G02C 9/00; G02C 11/12; G02C 2200/08; G02C 5/00; G02C 7/102; G02C 11/00; G02C 7/022; G02C 7/086; G02B 1/04; G02B 1/041; G02B 1/11; G02B 1/115; G02B 5/223; G02B 5/23; G02B 1/10; G02B 5/208; G02B 1/14; G02B 2027/0118; G02B 27/0172; G02B 5/22; G02B 5/28; G02B 5/3083; G02B 1/005; G02B 1/118; G02B 2027/0112; G02B 2027/0138; G02B 2027/014; G02B 2027/0178; A61F 9/022; A61F 9/023; A61F 9/029; A61F 9/067; A61F 2/1613; A61F 2002/1696; A61F 2002/16965; A61F 2/16; A61F 2/1618; A61F 2/1654; A61F 2/1659; A61F 9/027; A61F 9/028; A61F 9/045; A61F 9/061
See application file for complete search history.

(56) References Cited

U.S. PATENT DOCUMENTS

| | | | | |
|---|---|---|---|---|
| 2,233,698 A * | 3/1941 | Girouard | ............... | G02C 5/12 2/206 |
| 4,787,729 A * | 11/1988 | Ruffen | ............... | G02C 5/122 351/131 |
| 5,167,036 A * | 12/1992 | Daprato | ............... | G02C 5/12 2/13 |
| 2012/0036608 A1* | 2/2012 | Beliveau | ............... | A61F 9/029 2/9 |
| 2017/0266049 A1* | 9/2017 | Chou | ............... | G02C 9/00 |

FOREIGN PATENT DOCUMENTS

TW M544015 U 6/2017

* cited by examiner

*Primary Examiner* — William R Alexander
*Assistant Examiner* — Sharrief I Broome
(74) *Attorney, Agent, or Firm* — Rosenberg, Klein & Lee

(57) ABSTRACT

A nasal mask structure for eyeglasses is disclosed herein. It comprises a main body having a clamping part corresponding to a bridge of the eyeglasses and two engaging parts at two sides thereof for connecting two frames of the eyeglasses.

2 Claims, 8 Drawing Sheets

NASAL MASK STRUCTURE FOR EYEGLASSES

BACKGROUND OF THE INVENTION

1. Field of the Invention

The present invention relates to a nasal mask structure for eyeglasses which comprises a clamping part and two engaging parts for easily assembling to two frames of the eyeglasses.

2. Description of Related Art

Generally, people wear the sunglasses or snow goggles to protect the eyes from wind, snow and injuries when they go out, walk, climb and engage in outdoor activities, e.g. riding a high-speed locomotive and the like.

In order to protect the user's nose and prevent the user's nose from poor breathing or even frostbite due to the wind and snow, the frame of the snow goggle is provided with a nasal mask corresponding to the user's nose for covering and protection.

For instance, the Taiwan patent TWM544015 (U), issued on 21 Jun. 2017, disclosed a snow goggle having a nasal mask replacement structure. It mainly comprises a frame and a nasal mask. The frame is provided with an assembly portion at a middle section thereof and having a receiving slot, and a pressing unit corresponding to the assembly portion and having a retractable rod corresponding to the receiving slot. The nasal mask is provided with an inserting part for corresponding to the receiving slot of the assembly portion of the frame, and the inserting part is provided with a recess for correspondingly engaging with the retractable rod of the pressing unit.

In addition to the snow goggle used in outdoor activities, there are other types of goggles such as wind-shielded glasses or sunglasses that protect the eyes from the sun. Although the user's eyes are well protected by the glasses or goggles, the nose is easily sunburned because it is not shielded by the glasses, so the overall structural design of the conventional glasses or goggles still needs to be improved.

SUMMARY OF THE INVENTION

In view of the above-mentioned problems, the object of the present invention is to provide a nasal mask structure for eyeglasses which comprises a clamping part and two engaging parts for easily assembling to two frames of the eyeglasses.

Disclosed herein is a nasal mask structure for eyeglasses. It mainly comprises a main body having a clamping part corresponding to a bridge of the eyeglasses and two engaging parts respectively and correspondingly disposed on two lenses of the eyeglasses.

Accordingly, the nasal mask structure of the present invention can be assembled and positioned on the eyeglasses easily by engagement so as to block ultraviolet rays, strong winds, and the like and achieve the effect of protecting the nose.

According to an embodiment of the present invention, the clamping part has an upper hook for hooking at an upper edge of the bridge and a lower hook for hooking at a lower edge of the bridge.

According to an embodiment of the present invention, the main body has two engaging parts respectively and correspondingly disposed on two frames of the eyeglasses, and each of the two engaging parts has an orientation hook for engaging with margins of the two frames of the eyeglasses.

According to an embodiment of the present invention, each of the two engaging parts has an orientation hook for engaging with margins of the two lenses of the eyeglasses.

According to an embodiment of the present invention, the upper hook is correspondingly engaged with an upper engaging slot disposed at the upper edge of the bridge for positioning, and the lower hook is correspondingly engaged with a lower engaging slot disposed at the lower edge of the bridge for positioning.

DETAILED DESCRIPTION OF THE PREFERRED EMBODIMENT

Hereinafter, an exemplary embodiment of the present invention will be described in detail with reference to the accompanying drawings.

Figure 1:
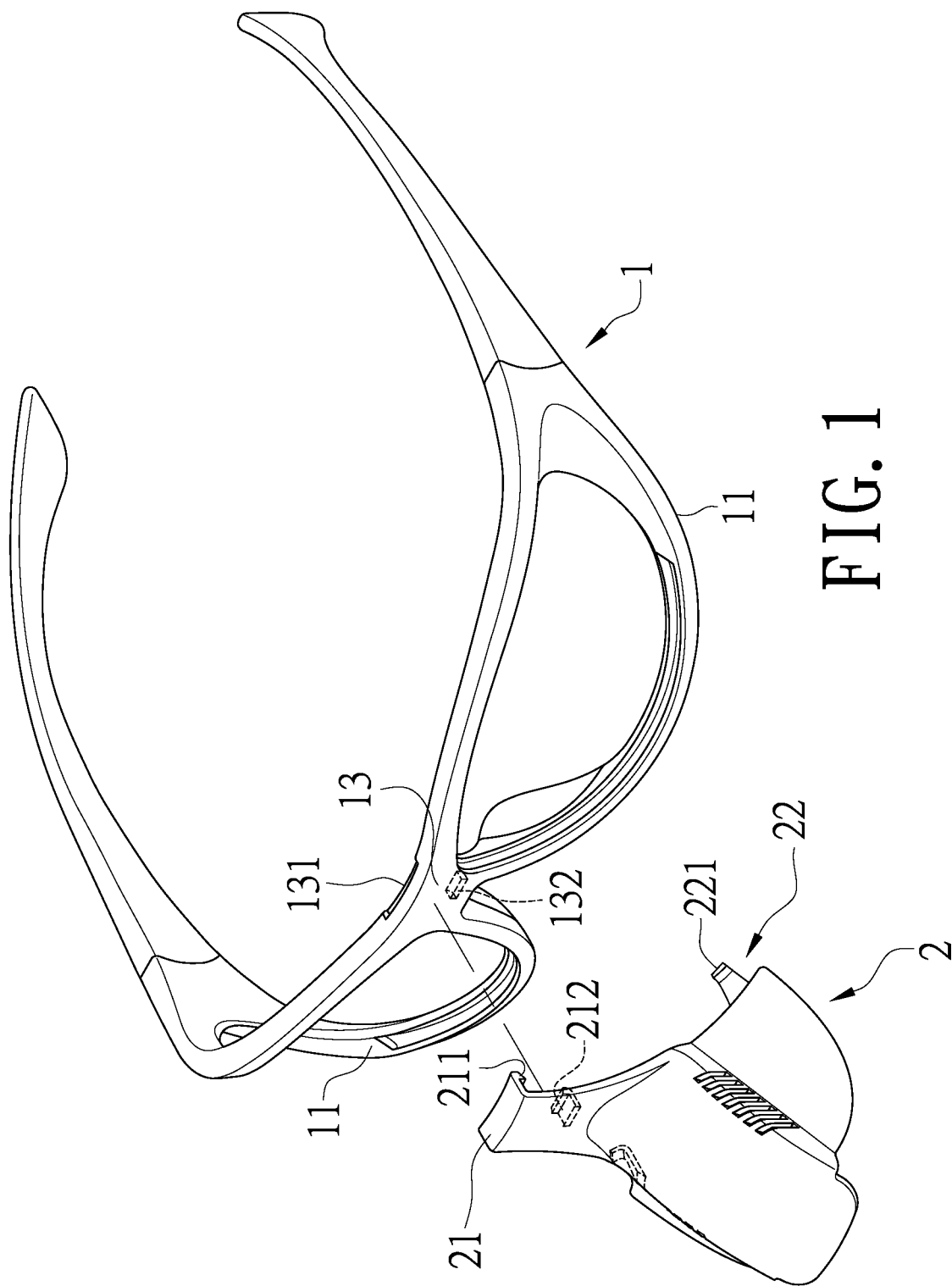
FIG. 1 is an exploded view showing a first embodiment for a nasal mask structure for eyeglasses according to the present invention.
Figure 2:
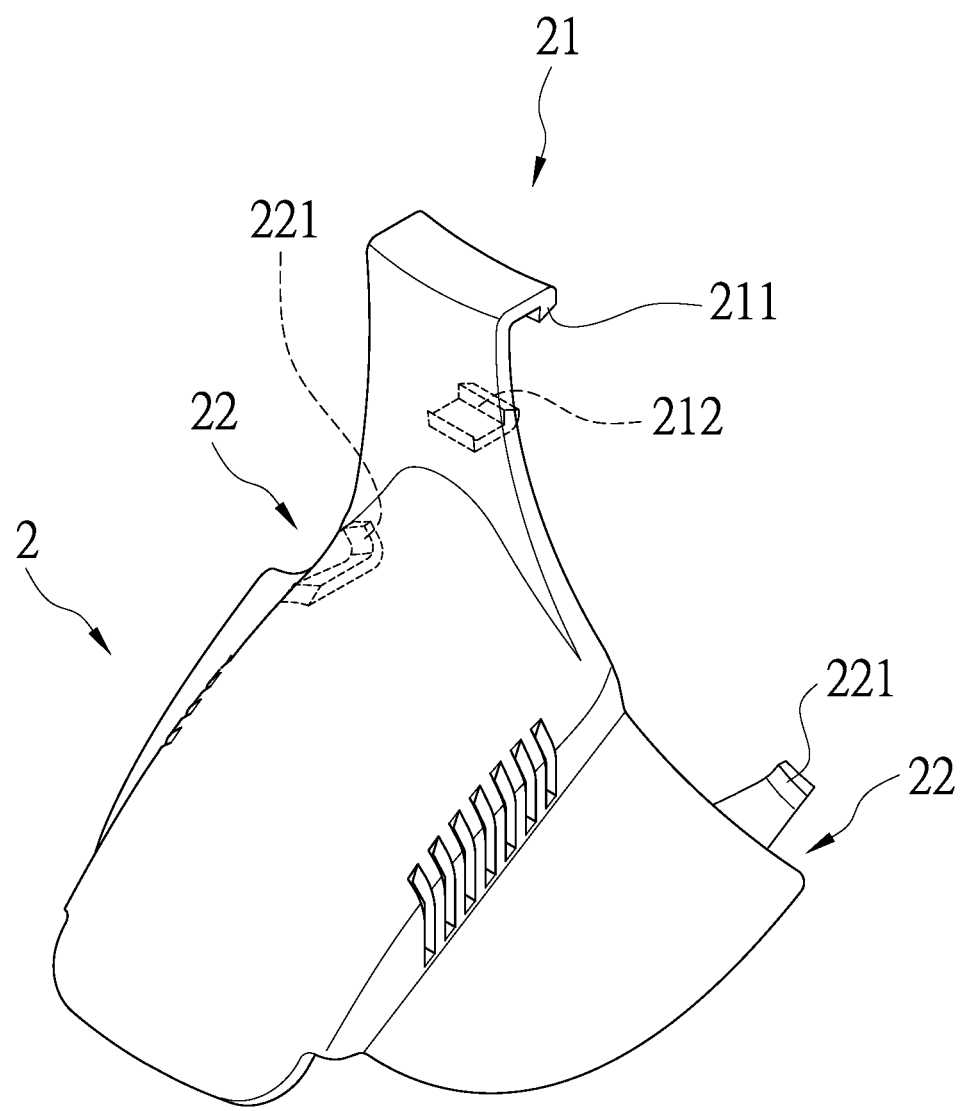
FIG. 2 is a stereogram showing a nasal mask structure for eyeglasses according to the present invention.
Figure 3:
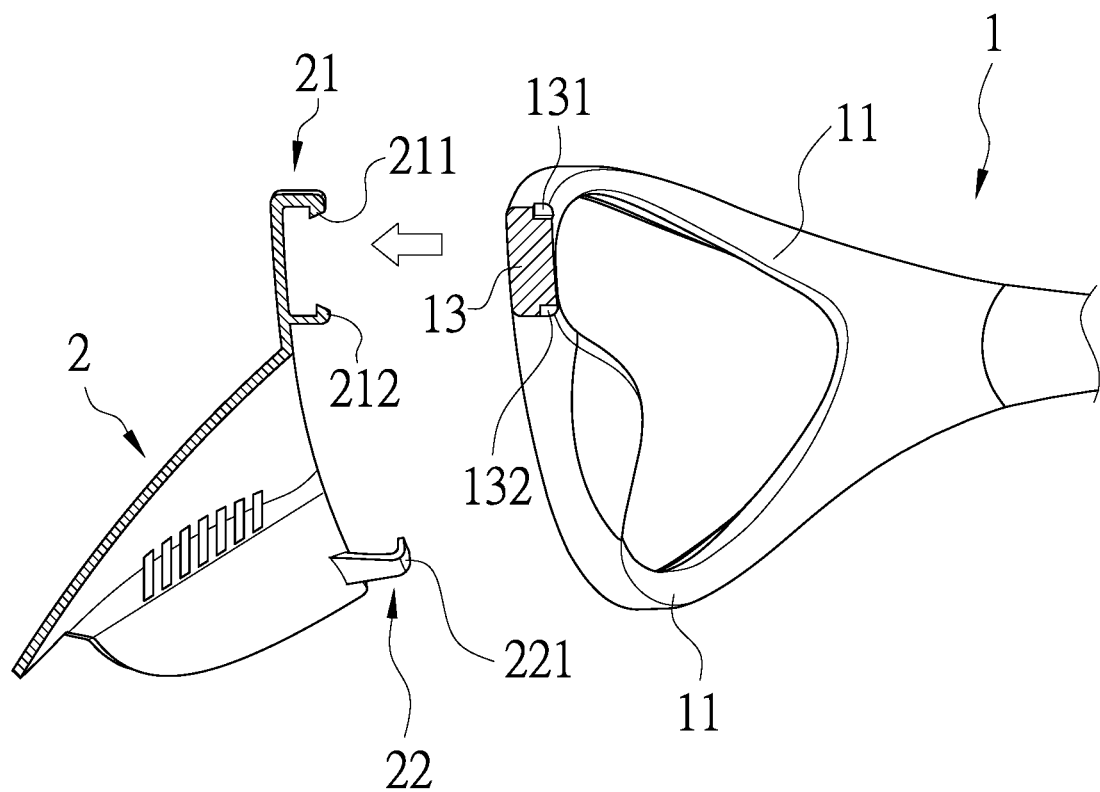
FIG. 3 is a cross-sectional view showing the first embodiment for the nasal mask structure for eyeglasses according to the present invention.
Figure 4:
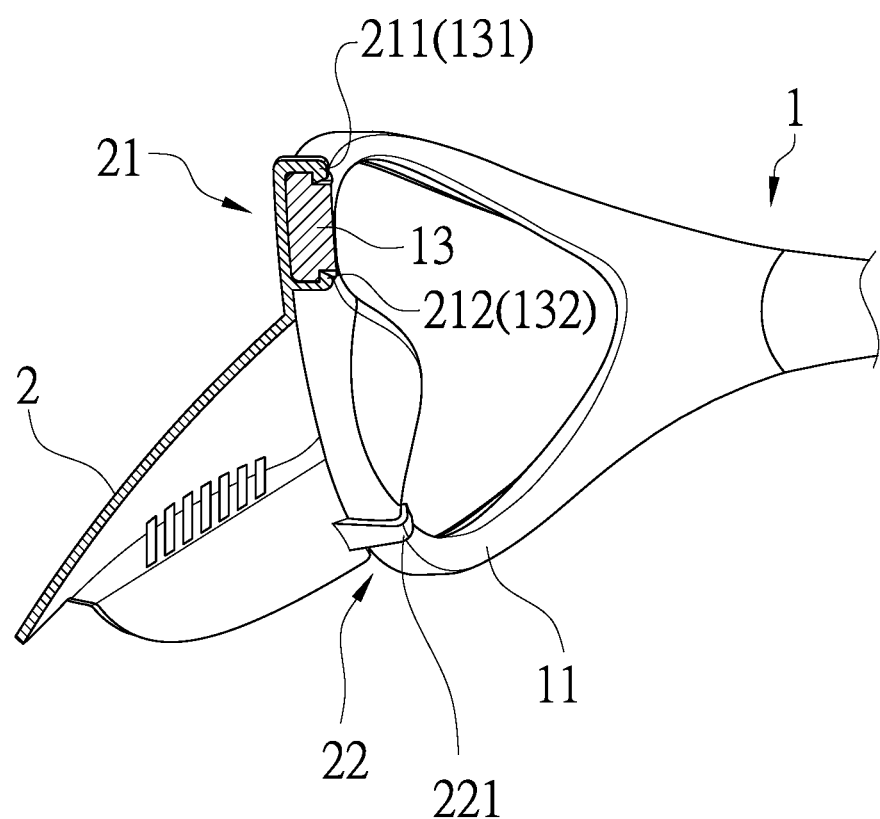
FIG. 4 is a cross-sectional view showing the first embodiment for the nasal mask structure for eyeglasses in assembly according to the present invention.
Figure 5:
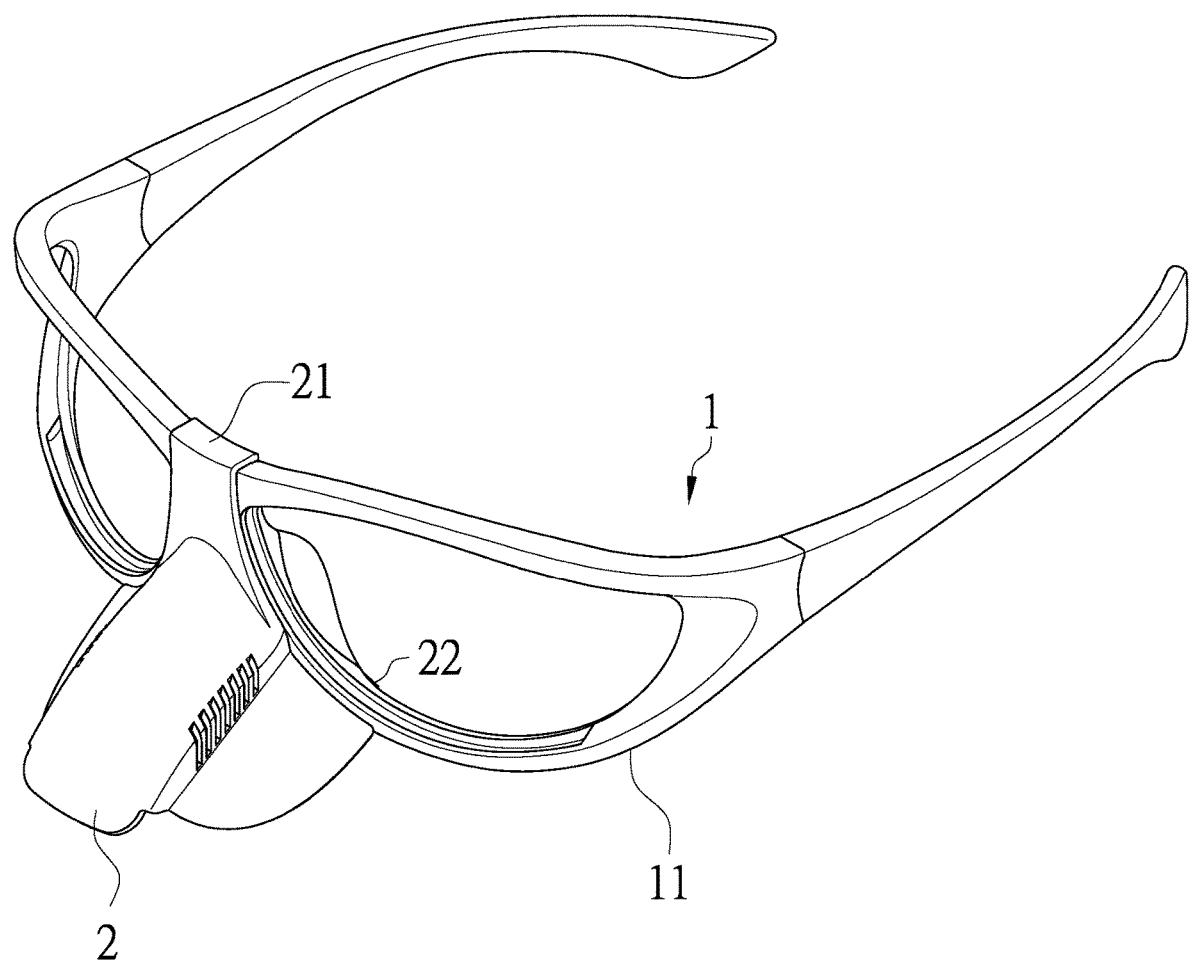
FIG. 5 is a stereogram showing the first embodiment for the nasal mask structure for eyeglasses in assembly according to the present invention.

As showed in FIG. 1 and FIG. 2, a nasal mask structure for eyeglasses of the present invention mainly comprises a main body (2) for assembling to the eyeglasses (1). The eyeglasses (1) comprises two frames (11), two lenses (12) respectively disposed on the two frames (11) and a bridge (13) between the two frames (11). The combination of the main body (2) and the eyeglasses (1) of the present invention has two implementation as described below.

Embodiment 1

As showed in FIG. 1 to FIG. 5, a first embodiment for a nasal mask structure for eyeglasses according to the present invention is disclosed. A main body (2) is used for assembling to the eyeglasses (1) to cover the nose. The main body (2) is provided with a clamping part (21) corresponding to a bridge (13), and the clamping part (21) is further provided with an upper hook (211) for hooking at an upper edge of the bridge (13) and a lower hook (212) for hooking at a lower edge of the bridge (13). Two sides of the main body (2) is also provided with two engaging parts (22) corresponding to two frames (11), and each of the two engaging parts (22) is further provided with an orientation hook (221) for engaging with margins of the two frames (11).

In a practical use of the first embodiment as showed in FIG. 1 to FIG. 5, the upper edge of the bridge (13) is provided with an upper engaging slot (131) corresponding to the upper hook (211) for positioning, and the lower edge of the bridge (13) is provided with a lower engaging slot (132) corresponding to the lower hook (212) for positioning. In such a case, the clamping part (21) of the main body (2) is firmly positioned on the bridge (13) by the upper engaging slot (131) engaging with the upper hook (211) and the lower engaging slot (132) engaging with the lower hook (212). Furthermore, the two orientation hooks (221) of the two engaging parts (22) are correspondingly engaged with margins of the two frames (11) for further positioning. Accordingly, the first embodiment that the two orientation hooks (221) of the two engaging parts (22) engage with margins of the two frames (11) is suitable for assembly with general full-frame glasses to achieve a stable assembly.

Embodiment 2

Figure 6:
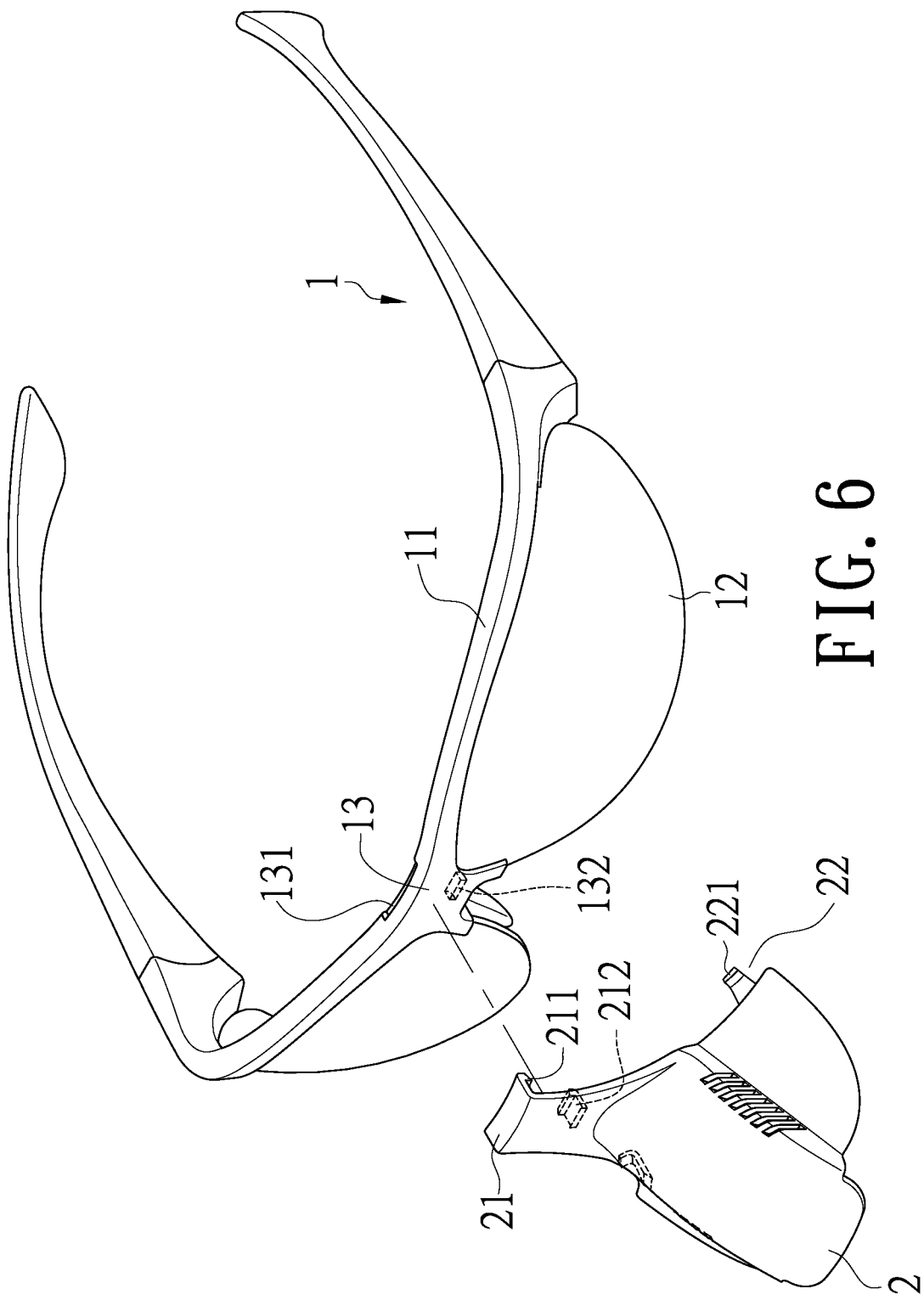
FIG. 6 is an exploded view showing a second embodiment for a nasal mask structure for eyeglasses according to the present invention.
Figure 7:
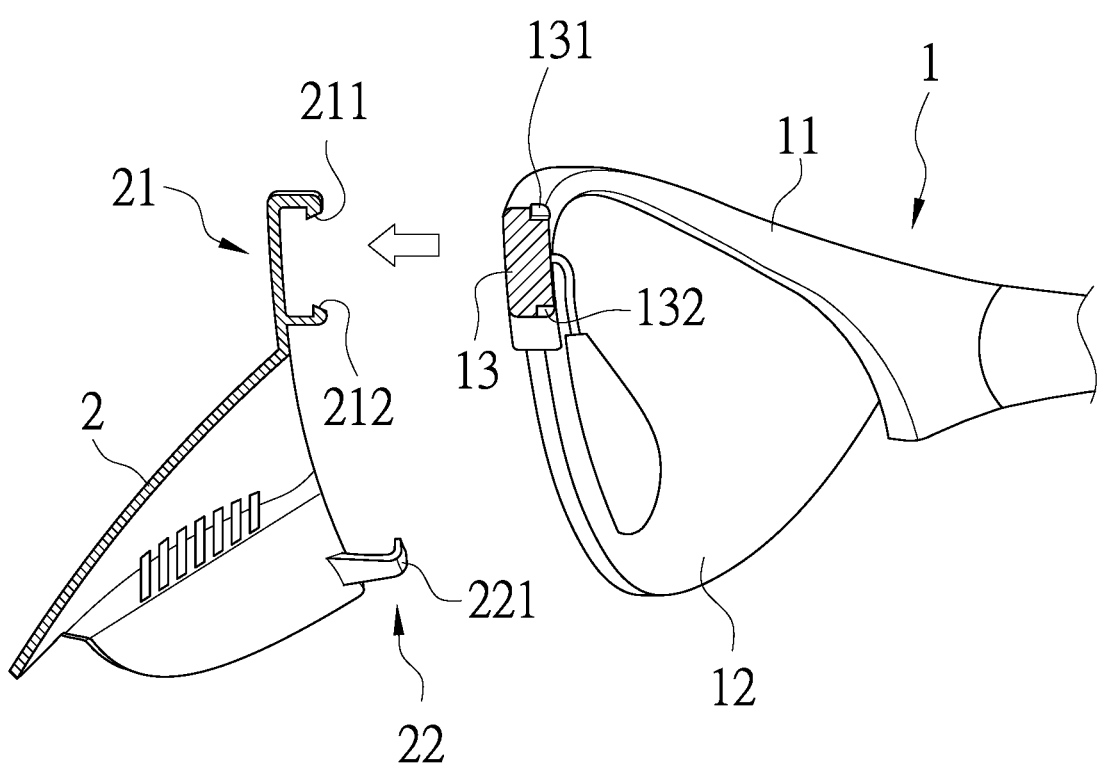
FIG. 7 is a cross-sectional view showing the second embodiment for the nasal mask structure for eyeglasses according to the present invention.
Figure 8:
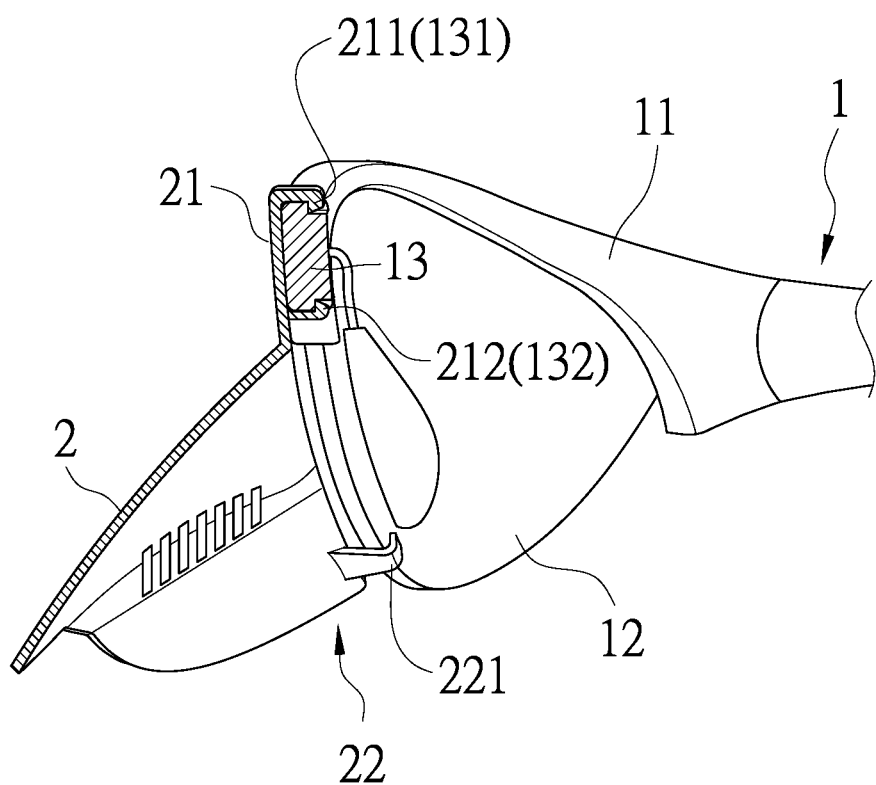
FIG. 8 is a cross-sectional view showing the second embodiment for the nasal mask structure for eyeglasses in assembly according to the present invention.

As showed in FIG. 6 to FIG. 8, a second embodiment for a nasal mask structure for eyeglasses according to the present invention is disclosed. A main body (2) is used for assembling to the eyeglasses (1) to cover the nose. The main body (2) is provided with a clamping part (21) corresponding to the bridge (13), and the clamping part (21) is further provided with an upper hook (211) for hooking at an upper edge of the bridge (13) and a lower hook (212) for hooking at a lower edge of the bridge (13). Two sides of the main body (2) is also provided with two engaging parts (22) corresponding to two lenses (12), and each of the two engaging parts (22) is further provided with an orientation hook (221) for engaging with margins of the two lenses (12).

In a practical use of the first embodiment as showed in FIG. 6 to FIG. 8, the upper edge of the bridge (13) is provided with an upper engaging slot (131) corresponding to the upper hook (211) for positioning, and the lower edge of the bridge (13) is provided with a lower engaging slot (132) corresponding to the lower hook (212) for positioning. In such a case, the clamping part (21) of the main body (2) is firmly positioned on the bridge (13) by the upper engaging slot (131) engaging with the upper hook (211) and the lower engaging slot (132) engaging with the lower hook (212). Furthermore, the two orientation hooks (221) of the two engaging parts (22) are correspondingly engaged with the margins of the two lenses (12) for further positioning. Accordingly, the second embodiment that the two orientation hooks (221) of the two engaging parts (22) engage with the margins of the two lenses (12) is suitable for assembly with general half-frame glasses to achieve a stable assembly.

Compared with the technique available now, the present invention has the following advantages:

1. The present invention achieves the effects of protecting the nose, e.g. blocking ultraviolet rays, strong winds, and the like.

2. The present invention has the clamping part and the two engaging parts on the main body, so it achieves the effect of being stably positioned on the eyeglasses without falling off.

3. The present invention can be positioned on the frames or the lenses of the eyeglasses to apply to different eyeglasses, so it achieves increased convenience in use and practicality of overall implementation.

What is claimed is:

1. A nasal mask structure for eyeglasses, comprising:
a main body for assembling to the eyeglasses and being configured to overlay a wearer's nose and block ultraviolet light and wind therefrom, the main body having a clamping part corresponding to a bridge of the eyeglasses and two engaging parts respectively disposed on two sides thereof in respective correspondence to two lens frame portions of the eyeglasses, wherein the clamping part has an upper hook correspondingly engaged with an upper engaging slot formed in an upper edge of the bridge of the eyeglasses for positioning, and wherein the clamping part has a lower hook correspondingly engaged with a lower engaging slot formed in a lower edge of the bridge of the eyeglasses for positioning, and each of the two engaging parts has an orientation hook engaged with an outer margin of a corresponding one of the two lens frames.

2. A nasal mask structure for eyeglasses, comprising:
a main body for assembling to the eyeglasses and being configured to overlay a wearer's nose and block ultraviolet light and wind therefrom, the main body having a clamping part corresponding to a bridge of the eyeglasses and two engaging parts respectively disposed on two sides thereof in respective correspondence to two lenses of the eyeglasses, wherein the clamping part has an upper hook correspondingly engaged with an upper engaging slot formed in an upper edge of the bridge of the eyeglasses for positioning, and wherein the clamping part has a lower hook correspondingly engaged with a lower engaging slot formed in a lower edge of the bridge of the eyeglasses for positioning, and each of the two engaging parts has an orientation hook engaged with an outer margin of a corresponding one of the two lenses.

* * * * *